_(United States Patent [19])_

Rosenau

[11] 4,259,633
[45] Mar. 31, 1981

[54] METHOD AND APPARATUS FOR MEASURING THE MOISTURE CONTENT OF WOOD

[75] Inventor: Clifford M. Rosenau, Willow Street, Pa.

[73] Assignee: Armstrong Cork Company, Lancaster, Pa.

[21] Appl. No.: 927,887

[22] Filed: Jul. 25, 1978

[51] Int. Cl.³ .................... G01R 27/02; G01R 27/26
[52] U.S. Cl. ............................ 324/65 R; 324/61 R
[58] Field of Search ...................... 324/65 R, 61 R

[56] References Cited

U.S. PATENT DOCUMENTS

| | | | |
|---|---|---|---|
| 2,673,327 | 3/1954 | Morelock | 324/65 R |
| 2,958,820 | 11/1960 | Volk | 324/65 R |
| 2,984,784 | 5/1961 | Mead | 324/65 R |
| 2,987,672 | 6/1961 | March et al. | 324/65 R X |
| 3,070,746 | 12/1962 | Moore et al. | 324/65 R |
| 3,209,248 | 9/1965 | Siefert | 324/65 R |
| 3,217,250 | 11/1965 | Goemann | 324/65 R |
| 3,281,681 | 10/1966 | Stevenson | 324/65 R |
| 3,427,537 | 2/1969 | Osborne | 324/65 R |
| 3,766,471 | 10/1973 | Pullman | 324/65 R |
| 3,807,055 | 4/1974 | Kraxberger | 34/16.5 |
| 3,841,316 | 10/1974 | Meyer | 324/65 R UX |

OTHER PUBLICATIONS

Lin, R. T., "A Study of Electrical Conduction in Wood", Forest Products Journal, vol. 15, Nov. 1965, pp. 506-514.

Primary Examiner—Ernest F. Karlsen
Attorney, Agent, or Firm—John J. Horn; Daniel DeJoseph

[57] ABSTRACT

An improvement in devices for determining the moisture content of lumber by measuring the electrical resistance of the wood. A biasing system is provided so that the voltage supplied to the electrical contacts disposed in the wood may be adjusted. This arrangement allows for corrections to be made in the electrical operation of the device, which corrections compensate for anomalous properties of the wood.

1 Claim, 1 Drawing Figure

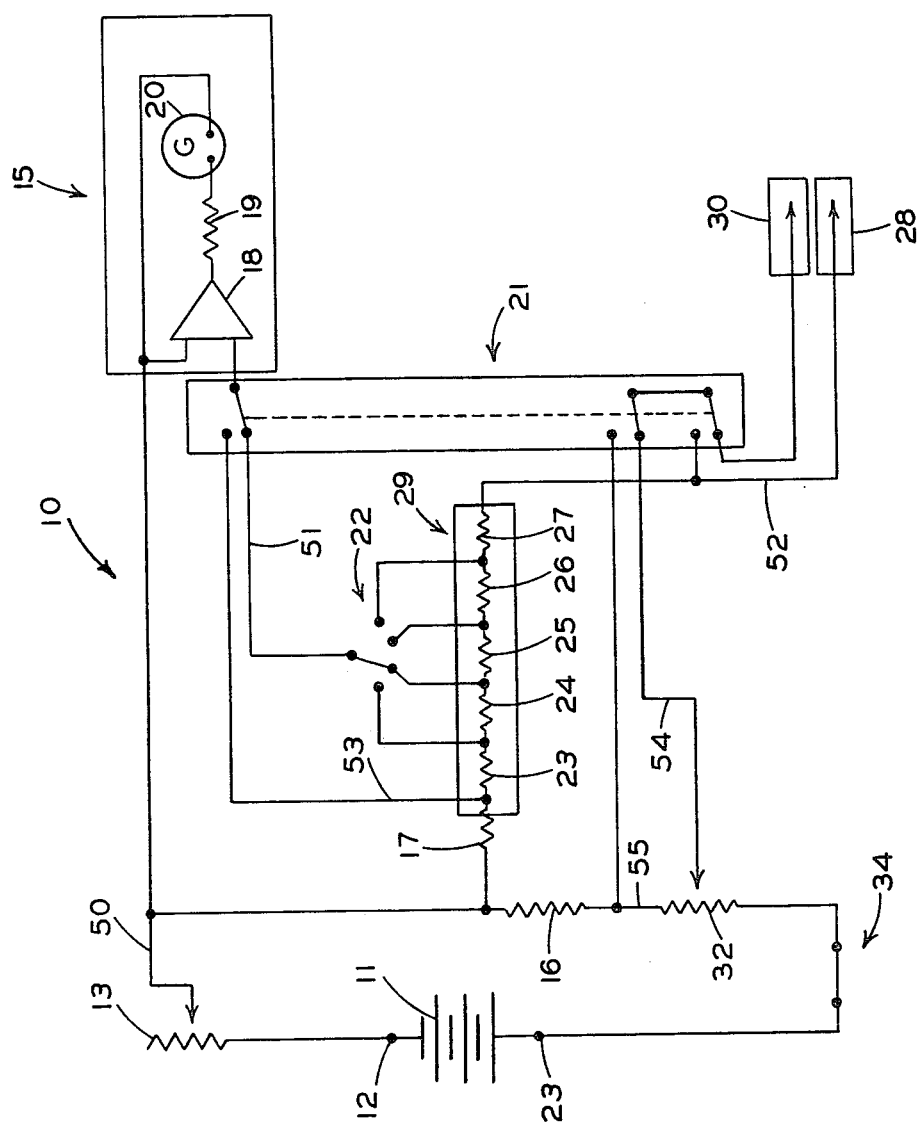

METHOD AND APPARATUS FOR MEASURING THE MOISTURE CONTENT OF WOOD

BACKGROUND OF THE INVENTION

The present invention relates to the determination of the moisture content of wood and, more particularly, to such determination by measuring electrical resistance through the wood.

During lumber processing operations, it is often necessary to determine the moisture content of the wood undergoing processing. To accomplish this function meter-type devices have been developed which determine the moisture content of wood based on the principle that the electrical resistance of wood varies with the moisture content. In these conventional devices, a DC voltage source is provided which develops a voltage potential across a pair of electrodes which are contacted with the wood at an appropriate distance from one another. The electrical properties exhibited by the circuit are dependent on the resistance of the wood. Measurements of one or more of the electrical properties of the circuit are used to determine the resistance of the wood, and this resistance is then correlated with a wood moisture content. These devices provide a rapid and convenient method of ascertaining wood moisture content. However, these devices are generally acknowledged to be somewhat inaccurate and especially unreliable at moisture levels above 30%.

Accordingly, it is a principal object of the present invention to provide a device for measuring wood moisture content which operates with improved accuracy and greater reliability at moisture levels above 30%.

It is another object of the present invention to provide a meter-type device for measuring wood moisture content which is of simple and durable construction; is easy, rapid, and convenient to use; and is otherwise well adapted to the purposes for which the same is intended.

SUMMARY OF THE INVENTION

An improved meter-type device for determining the moisture content of lumber by measuring the electrical resistance through the wood. A voltage source is connected to a set of electrodes adapted to be contacted with the wood whose moisture content is to be measured. A meter for measuring one or more of the electrical properties of the circuit is connected to the circuit. A variable resistance is coupled with the voltage source and one of the electrodes. In operation, electrical contact is made from the voltage source through the electrodes across the wood. The voltage potential supplied by the voltage source is maintained generally above a certain critical level and is corrected to compensate for anomalous properties of the individual type of wood being tested. One of the electrical properties of the circuit is measured and displayed on the meter. The electrical property measured is correlated with wood moisture content.

BRIEF DESCRIPTION OF THE DRAWING

The FIGURE shows a circuit diagram of the present invention.

DESCRIPTION OF THE PREFERRED EMBODIMENT

Referring now to the FIGURE, there is shown a circuit 10 embodying the present invention. Voltage source 11 is a battery providing approximately 45 volts DC of electromotive force. Terminal 12 of source 11 is connected to calibrating potentiometer 13 which provides about 500 ohms resistance at full range. Potentiometer 13 is connected via electrical line 50 to meter 15, reference resistor 16, and calibration resistor 17. Resistors 16 and 17 are approximately 4,000 and 2.0 ohms, respectively. Meter 15 is preferably a conventional 0–5 mv range voltmeter having approximately 10 megaohms of input resistance. Alternatively, meter 15 may be constructed of base components to form the voltmeter desired. An amplifier 18 would be connected in series with a resistor 19 and a galvanometer 20. Amplifier 18 would preferably be a low-drift, linear instrumentation amplifier having approximately 800 volts/volt gain; resistor 19 would be approximately a 97,000 ohm resistor; and galvanometer 20 would be a conventional 0–50 microampere galvanometer having approximately 3,000 ohms of input resistance. Meter 15 is also connected through switch 21 via line 51 to range selector switch 22. Selector switch 22 couples the meter 15 through one or more scale resistors 23–27 to electrode 28 via line 52. Scale resistors 23–27 are peferably 2; 16; 230; 10,000; and 15,000 ohms, respectively. Scalea resistors 23–27 are connected in series to provide a voltage divider network 29 which may be tapped into various points by selector switch 22. Network 29 is connected to calibration resistor 17 via line 53 at its end opposite its connection to electrode 28 via line 52. Electrode 30 is connected to potentiometer 32 through switch 21 via line 54. Potentiometer 32 is approximately a 300 ohm resistor adapted so that it may be contacted at an electrically intermediate point. Potentiometer 32 is connected at one end to reference resistor 16 via line 55 and at the opposite end to terminal 33 of battery 11 through switch 34. Line 54 contacts potentiometer 32 at an intermediate point variable so that the resistance between line 55 and line 54 may be adjusted. Switch 21 is a two position gang operating switch for use in calibrating the meter 15. Switch 34 is a two position switch which functions as the On-Off switch for the circuit 10.

In operation, the meter 15 may be calibrated by turning switch 21 to the calibration position once switch 34 is in the On position. When switch 21 is in the calibration position, meter 15 is disconnected from line 51 and connected to line 53 and electrode 30 is disconnected, while line 55 is connected to line 52. Consequently, only source 11, network 29, resistors 16 and 17, potentiometers 13 and 32, and meter 15 are actively included in the circuitry. Since network 29, resistor 16 and 17, and potentiometer 32, as connected, have predetermined values potentiometer 13 may be used to zero the meter 15 and adjust the voltage drop across reference resistor 16 to a standard value, preferably 40 volts. After calibration, the electrodes 28 and 30 should be contacted with the sample of wood to be tested. Electrodes 28 and 30 should preferably be stainless steel pins; which pins may be driven into the wood at an appropriate distance from one another, such as two inches, on a line parallel with the grain of the wood; and which pins may be driven into the wood to an appropriate depth, such as one ane a quarter inches. The switch 21 should be turned to the operations position. Potentiometer 32 should be adjusted in accordance with the species of wood being tested. Range selector switch 22 should then be moved to a position which gives an on-scale meter reading. The face of meter 15 may preferably be calibrated directly in wood moisture content for the ranges corresponding to the various positions of switch 22. In the case of the present device as described, the moisture content ranges for the various switch positions would be, approximately, position #1-7 to 10%, #2-10 to 15%, #3-15 to 25%, #4-25 to 90%. In electrical operation, resistor 16 and potentiometer 32 establish a voltage across electrodes 28 and 30 and network 29. The wood sample and the network 29 act as voltage divider, the voltage drop across the network 29 and its components varying according to the resistance offered by the wood sample. Meter 15 measures the voltage drop across various sets of scale resistors in network 29 providing thereby an indication of the resistance offered by wood sample and the moisture content of the wood. Potentiometer 32 provides a variable point of electrical connection for electrode 30 relative to the voltage drop provided by battery 11 through resistor 16 and potentiometer 32. Potentiometer 32 acts as a voltage divider providing an adjustable voltage drop across the wood sample and network 29. This is important because it has been discovered that various species of wood react differently to electrical currents exhibiting certain anomalous properties. When a test voltage is applied across a sample of wood, the wood commonly exerts a "reverse" electromotive force. This reverse voltage effect increases with increasing applied voltage up to some maximum value, different for different wood species. This maximum value, for example two volts in the case of red oak, appears to be attained when the applied voltage reaches about twice the reverse voltage effect. Once the applied voltage reaches this critical level, usually about 4-5 volts, the reverse voltage effect remains essentially constant with increasing voltage. In the range of voltages developed in battery powered devices, serious errors are introduced by not accounting for reverse voltage effects. The present invention takes accout of the above described reverse voltage effects by generally applying voltages to the wood samples being tested above or at the critical level for developing maximum reverse voltage effects, and by adjusting the voltage applied to the wood sample to correct for reverse voltage effects inherent in different wood species. The foregoing provisions of the present invention permit meaningful and accurate moisture measurements even at high moisture levels.

What is claimed is:

1. A method of determining the wood moisture content of different species of woods comprising the steps of:
   (a) connecting a source of voltage potential through a set of electrodes across a sample of a particular wood species whose moisture content is to be measured;
   (b) correcting the voltage potential supplied by said source to compensate for reverse voltage effects inherent in each individual type of wood species being tested, said voltage potential being applied at or above the critical level for the development of reverse voltage effect, which critical level is that voltage potential above which the reverse voltage effect of the wood species remains essentially constant;
   (c) measuring one or more of the electrical properties of the circuit connected to the source and electrodes;
   (d) correlating the measured electrical properties of said circuit with wood moisture content.

* * * * *